(12) United States Patent
Hehle et al.

(10) Patent No.: US 9,779,218 B2
(45) Date of Patent: Oct. 3, 2017

(54) METHOD FOR MODEL-BASED DETERMINATION OF A TEMPERATURE DISTRIBUTION OF AN EXHAUST GAS POST-TREATMENT UNIT

(75) Inventors: Marc Hehle, Constance (DE); Ralf Müller, Deggenhausertal (DE); Jens Niemeyer, Friedrichshafen (DE); Jörg Remele, Hagnau (DE); Guido Schäffner, Horgenzell (DE); Holger Sinzenich, Markdorf (DE); Tim Späder, Kressbronn (DE)

(73) Assignee: MTU Friedrichshafen GmbH, Friedrichshafen (DE)

( * ) Notice: Subject to any disclaimer, the term of this patent is extended or adjusted under 35 U.S.C. 154(b) by 1029 days.

(21) Appl. No.: 13/985,923

(22) PCT Filed: Feb. 7, 2012

(86) PCT No.: PCT/EP2012/000558
§ 371 (c)(1),
(2), (4) Date: Oct. 10, 2013

(87) PCT Pub. No.: WO2012/110210
PCT Pub. Date: Aug. 23, 2012

(65) Prior Publication Data
US 2014/0032189 A1 Jan. 30, 2014

(30) Foreign Application Priority Data
Feb. 16, 2011 (DE) .................. 10 2011 011 426
May 27, 2011 (DE) .................. 10 2011 103 346

(51) Int. Cl.
*G06F 19/00* (2011.01)
*F01N 3/20* (2006.01)
(Continued)

(52) U.S. Cl.
CPC .......... *G06F 19/701* (2013.01); *F01N 3/208* (2013.01); *F01N 9/005* (2013.01); *F01N 11/005* (2013.01);
(Continued)

(58) Field of Classification Search
USPC .................................................. 60/274, 276
See application file for complete search history.

(56) References Cited

U.S. PATENT DOCUMENTS

| 4,859,639 A | 8/1989 | Sterzel |
| 5,628,186 A | 5/1997 | Schmelz |

(Continued)

FOREIGN PATENT DOCUMENTS

| CN | 101466922 A | 6/2009 |
| DE | 100 36 942 A1 | 5/2002 |

(Continued)

OTHER PUBLICATIONS

PCT International Search Report dated Jun. 6, 2012 for PCT/EP2012/000558.
English Abstract for CN 101466922.

*Primary Examiner* — Aniss Chad
(74) *Attorney, Agent, or Firm* — Reising Ethington (57) ABSTRACT

In a method for a model-based determination of a temperature distribution of an exhaust gas post-treatment unit, a differentiation is made between steady operating states and non-steady operating states by taking into account the axial and the radial temperature distribution, and, on the basis of virtual segmentation of the post-treatment unit, in particular the radial heat transfer to the surroundings is taken into account in the model-based determination for steady operating states, and for non-steady operating states the heat transfer from the exhaust gas which flows axially through (Continued)

the post-treatment unit to the segments is taken into account by a heat transfer coefficient k.

12 Claims, 5 Drawing Sheets

(51) Int. Cl.
    *F01N 9/00*     (2006.01)
    *F01N 11/00*     (2006.01)

(52) U.S. Cl.
    CPC ......... *F01N 2900/0406* (2013.01); *F01N 2900/1602* (2013.01); *F02D 2200/0804* (2013.01); *Y02T 10/24* (2013.01); *Y02T 10/47* (2013.01)

(56) References Cited

U.S. PATENT DOCUMENTS

| | | | |
|---|---|---|---|
| 5,930,993 A * | 8/1999 | Kammann | F01N 9/005 60/274 |
| 6,119,448 A | 9/2000 | Emmerling et al. | |
| 6,276,128 B1 * | 8/2001 | Kammann | F01N 11/002 60/274 |
| 7,028,465 B2 | 4/2006 | Ripper et al. | |
| 7,093,427 B2 | 8/2006 | van Nieuwstadt et al. | |
| 7,204,081 B2 | 4/2007 | Yasui et al. | |
| 8,061,122 B2 | 11/2011 | Chaineux et al. | |
| 8,191,357 B2 | 6/2012 | Doring et al. | |
| 8,196,390 B2 | 6/2012 | Lueders et al. | |
| 8,333,062 B2 | 12/2012 | Sun | |
| 8,865,615 B2 * | 10/2014 | Ito | B01J 35/04 502/262 |
| 2004/0098974 A1 * | 5/2004 | Nieuwstadt | B01D 53/9431 60/286 |
| 2010/0005781 A1 | 1/2010 | Schweizer | |

FOREIGN PATENT DOCUMENTS

| | | |
|---|---|---|
| DE | 103 05 451 A1 | 7/2004 |
| DE | 10301606 A1 | 7/2004 |
| DE | 10 2006 021303 A1 | 11/2007 |
| DE | 102006033929 A1 | 1/2008 |
| EP | 1334760 A2 | 8/2003 |
| EP | 2025388 A1 | 2/2009 |
| WO | WO-2009/040307 A1 | 4/2009 |

* cited by examiner

METHOD FOR MODEL-BASED DETERMINATION OF A TEMPERATURE DISTRIBUTION OF AN EXHAUST GAS POST-TREATMENT UNIT

CROSS REFERENCE TO RELATED APPLICATIONS

This application is a National Phase Application related to PCT/EP2012/000558 filed on Feb. 7, 2012, which application claims priority to DE 10 2011 011 426.2 filed on Feb. 16, 2011, and DE 2011 103 346.0 filed on May 27, 2011, which applications are incorporated herein by reference in their entirety.

TECHNICAL FIELD

The disclosure relates to a method for a model-based determination of a temperature distribution of an exhaust gas post-treatment unit, in particular of a catalytic converter, and in one exemplary arrangement, of an SCR catalytic converter or of a particle filter.

BACKGROUND

One known method, for example, from DE 10 36 942 B4 and is based on the fact that the average temperature, determined by means of the through-flow length of an exhaust gas post-treatment unit, for example a catalytic converter, does not give a sufficient basis, at any rate in the dynamic operating mode and with the associated non-homogeneous temperature distribution, for the adjustment of a system comprising an engine and the exhaust gas post-treatment unit in such a way that strict requirements made of the exhaust gas quality are satisfied with the necessary accuracy. Said requirements are to be met in that the exhaust gas post-treatment unit is divided in a model-based fashion in the axial direction into a number of disks, and in that the temperature of each disk is determined as a function of the temperature of the gas which flows against the disk. This is done under the assumption that the radial temperature distribution is constant and an adiabatic transfer of heat occurs between the exhaust gas and the disks of the exhaust gas post-treatment unit.

These assumptions lead, in turn, to certain inaccuracies, in particular as a result of the radial temperature gradient which forms contrary to the assumption, for which reason there is a need for these heat losses to be sensed and also taken into account on an approximate basis.

In a further method for the model-based determination of the temperature distribution of exhaust gas post-treatment units, which is known from DE 10 2009 046 771 A1, the axial temperature profile is initially determined at least in certain areas, and on the basis thereof a multi-dimensional temperature characteristic diagram is in turn calculated, at least in certain areas, on the basis of an analytical relationship. Said relationship can be based on various peripheral conditions such as, for example, an already known temperature and/or properties of the exhaust gas post-treatment unit which are significant for the transfer of heat. The position-dependent temperature can be obtained from the calculated temperature characteristic diagram as a result of which, by virtue of the axial temperature profile and the temperature characteristic diagram, in each case at least one temperature which occurs at any position within the exhaust gas post-treatment unit is obtained.

In DE 10 2006 021 303 B4, it is known, with respect to the acquisition of the temperature distribution in an exhaust gas post-treatment unit, to determine the axial temperature distribution by means of a dynamic heat model and to determine, by means of a kinematic model, the reaction heat which is generated during the exhaust gas post-treatment and results from the conversion of exhaust gas components. This is done in order to improve the quality of the determined temperature distribution with as little computational expenditure as possible. By determining the radial temperature distribution, which occurs perpendicular to the main flow, it is possible here to achieve a further improvement in quality on a case-by-case basis, but this in turn requires a relatively high level of computational expenditure.

DE 103 47 132 A1 discloses a method for estimating the quantity of ammonia stored in a urea-based SCR catalytic converter, on the basis of a dynamic catalytic converter model, and generates the estimate on the basis of measured and estimated values, wherein measured values are made available for this by $NO_x$ sensors and temperature sensors arranged upstream and downstream of the catalytic converter, said measured values also permitting information to be obtained about the proportion of ammonia in the exhaust gas downstream of the catalytic converter with respect to the $NO_x$ sensor located downstream of the catalytic converter on the basis of the cross-sensitivity to ammonia.

In a corresponding way, in EP 2 025 388 A1 sensors are used for determining measured values at an exhaust gas purification unit which operates with an SCR catalytic converter which is regulated in a model-based fashion with respect to the metering and storage of ammonia while taking into account the measured values.

DE 10 2007 045 263 A1 discloses a method for controlling the reducing agent supply into an exhaust gas post-treatment system of an internal combustion engine having an SCR catalytic converter, an SCR storage model, a control unit and a metering device, which method is intended to permit the quantity of reducing agent fed to the catalytic converter to be optimized independently of measurement variables which can be determined exclusively after the reduction reaction, and by which, with respect to the SCR catalytic converter, a breakthrough of reducing agent is to be avoided at all times. For the control unit, the nitrogen oxide crude emissions, storage temperature and storage filling level are determined as input variables. On the basis thereof, the maximum possible conversion rate is calculated and the ammonia consumed as reducing agent is calculated. Taking this as a basis, the quantity of nitrogen oxides and ammonia which escape via the catalytic converter and a regulating signal, which, when fed back to the SCR storage model, influences, via the storage model, the magnitude of the quantity of reducing agent which is to be sprayed in via the metering device, and which is taken into account together with the spraying quantity which is taken into account in the storage model, by means of the storage model for the storage filling level which forms an input variable for the control unit, are produced.

DE 10 2010 025 382 A1 presents an SCR catalytic converter onto which the reducing agent is sprayed upstream, and whose catalytic converter body is divided into disks transversely with respect to the direction of through-flow in a way analogous to DE 10 36 942 B4. This is done in order to be able to determine essential parameters for the function of the catalytic converter by means of disks as well as to be able to use changes which are significant for the overall result in the following disks, in particular with respect to their capability to store reducing agent, for the overall result.

SUMMARY

The present disclosure is intended to make it possible to adjust a system comprising an engine and an exhaust gas post-treatment unit, while taking into account a temperature distribution over a length of the exhaust gas post-treatment unit in a model-based fashion in such a way that compliance with predefined exhaust gas limiting values, in particular legally prescribed exhaust gas limiting values, can generally be ensured with acceptable expenditure.

This is achieved with a method recited in claim 1. The dependent claims specify expedient developments. Further details according to the disclosure can be found in the description and the drawings.

With respect to the exhaust gas post-treatment unit, which is preferably a catalytic converter, and in one particular arrangement an SCR catalytic converter, the disclosed method is based, with respect to the model-based determination of the temperature distribution and the $NH_3$ storage capability which relates thereto in the case of an SCR catalytic converter, on the division of the exhaust gas post-treatment unit into a plurality of segments in the lateral direction, in particular perpendicularly with respect to the direction of through-flow. In one exemplary arrangement, the segments are in the form of disks. For each of these disks, the temperature and the gas concentration in the model are calculated, wherein, with respect to the direction of through-flow, the output values of the respectively preceding disk serve as input values for the following disk.

A quantity balance is carried out for each of the disks in a known fashion. The results of these quantity balances are used to determine and influence the $NH_3$ storage filling level with respect to the example of the SCR catalytic converter as an exhaust gas post-treatment unit. Basically, by means of such a thermal model the volume of the SCR catalytic converter and the $NH_3$ quantity stored therein can be used better and taken into account in the metering of the reducing agent, that is to say with respect to the SCR catalytic converter of the quantity of $NH_3$, with the result that $NH_3$ breakthroughs at the optimized conversion rate can be avoided.

The division into disks therefore permits, with respect to an SCR catalytic converter, the concentration of the $NH_3$ and/or $NO_x$ to be determined virtually in a disk-specific fashion in accordance with a virtual sensor. The spatial resolution of the $NH_3$ storage quantity, of the $NO_x$ conversion and the $NH_3$ oxidation, corresponding to the division of the catalytic converter body into disks which is carried out in the model, means that at transient conditions the $NH_3$ storage volume is utilized better and the $NH_3$ slip is avoided.

The radial temperature distribution of the disk is modeled in accordance with the disk-specific axial temperature calculation and the monitoring by measuring an input temperature and output temperature for the exhaust gas post-treatment unit, that is to say in particular an SCR catalytic converter. For this purpose, each disk is cut up in the radial direction in a virtual fashion, corresponding to the axial division of the catalytic converter body into disks, whether these be rings which are concentric to one another, cubes or segments which are shaped in some other way, in particular shaped in a regular fashion and which are added together to form the respective disk-shaped body. The computing method for determining the temperature corresponds to that in the axial disk model, wherein, with respect to the ambient temperature which is measured in any case, the temperature losses which occur at the circumference are taken into account.

For the monitoring and calibration of the calculated radial temperature distribution, an additional temperature measurement is expediently provided on the outlet side in addition to the temperature measurement provided on the inlet and outlet sides, in particular by temperature sensors, by which the temperature is determined in areas which are spaced apart radially from the circumference on the outlet side, said temperature being determined, in particular, by arranging at least two temperature sensors provided in various radial positions. Instead of such an additional temperature measurement on the outlet side, it is also possible to work with just one sensor if, by virtue of its positioning with respect to the catalytic converter, said sensor is arranged in a position in which a corresponding mean temperature is present, for example at a relatively large axial distance from the catalytic converter.

Optimized use of the respective exhaust gas post-treatment unit is achieved by the combined radial and axial temperature modeling so that, for example in the case of catalytic converters, the possibility of reducing the installation space arises, and in the case of particle filters with active regeneration, a saving in fuel is also achieved by virtue of the optimized regeneration method associated therewith.

In the proposed method, the axial and radial temperature calculation for the respective disks of the body of the exhaust gas post-treatment unit which is divided in the model is carried out by taking into account the radial heat transfer to the circumference of the post-treatment unit by a heat transfer resistance $R_c$, and for the calculation of the transfer of heat from the exhaust gas to the material of the exhaust gas post-treatment unit, that is to say the segments of the post-treatment unit, by taking into account a heat transfer coefficient k.

This type of model-based determination of the temperature distribution of the exhaust gas post-treatment unit offers, an advantage that, by virtue of the procedure during the model-based determination of the temperature distribution, in the model output values are also made available which differ between a steady-state and a non-steady-state operating mode as a function of whether the exhaust gas temperatures measured upstream of the post-treatment unit at predefined time intervals change compared to a chronological mean value thereof.

In the proposed method it is assumed that a steady-state operating mode is present if the exhaust gas temperature, which is measured upstream of the exhaust gas post-treatment unit, in particular at regular time intervals, does not exhibit any relatively large deviations, above a predefined threshold value, from a chronological mean value. The threshold value can be defined in a variable fashion, that is to say as a function of further peripheral conditions, and is preferably, for example, at least 1° K, but can also lie within a range which constitutes a multiple thereof. If differences below the threshold value occur with respect to this steady-state operating mode for the average temperature measured downstream of the exhaust gas post-treatment unit from the averaged model temperature downstream of the exhaust gas post-treatment unit, the model is adapted, specifically in such a way that the heat transfer resistance $R_c$ is changed until correspondence occurs. In the described steady-state operating mode, the model is therefore adapted to the actual state, and this is done by changing the heat transfer resistance $R_c$.

The temperature model for an exhaust gas post-treatment unit is, in particular, an SCR temperature model, and therefore for the steady-state operating mode referred to above it is a control circuit which can be adjusted by changing the heat transfer resistance $R_c$ in order to reach the steady state. In practice, frequently occurring brief changes in the overflow conditions relating to the exhaust gas post-treatment unit, in particular to the catalytic converter, therefore remain substantially without influence on the model.

It is different when, in particular in the case of changes in load of a corresponding magnitude, the operational conditions for the exhaust gas post-treatment unit change, under certain circumstances additionally, with the effect that deviations of the exhaust gas temperature measured upstream of the exhaust gas post-treatment unit, that is to say, for example, upstream of the catalytic converter, occur with respect to a chronological mean value. For this case, it is assumed that the heat transfer resistance $R_c$ which is lower in the weighting remains the same during the comparatively short transient recovery process, but the changed conditions can be allowed for by changing the heat transfer coefficient k, which is dependent on the flow speed of the exhaust gas and therefore on the load.

The direction in which the k value, that is to say the heat transfer coefficient, is to be changed becomes apparent from the measured and calculated temperature profiles over time, determined from the average temperatures downstream of the exhaust gas post-treatment unit and the first two derivatives thereof. The k value is increased or decreased as a function of the relative timing of the inflection points, determined by maximum and minimum values, in the derivative curve.

Irrespective of whether the heat transfer resistance $R_c$ which takes into account the conditions of the surroundings of the post-treatment unit in the non-steady-state case, that is to say for the time period which is sensed as being non-steady-state, is considered as being constant, the changed outputting of heat into the surroundings is also taken into account in the non-steady-state case, since a changed heat flow occurs in the radial direction owing to the change in the internal temperatures of the disks.

The averaged model temperature which occurs downstream of the exhaust gas post-treatment unit, that is to say in particular downstream of the catalytic converter, in particular the SCR catalytic converter, is determined by virtue of the fact that the temperatures calculated for reference areas, that is to say, for example, rings of the last disk are averaged in accordance with their area components. Furthermore, it is assumed that the heat transfer coefficient k can be assumed at any rate to be known, and also correct, for certain load states and corresponding exhaust gas flow states, with the result that in this respect it is possible to assume the same state of affairs for the steady-state situation and for the non-steady-state situation, and a respectively identical reference basis is provided for the adaptation of the model, by changing the k value in the non-steady-state situation. In the non-steady-state situation it is possible that, in addition to the adaptation of the SCR model, the quantity of $NH_3$ which is to be fed in is changed and/or, if appropriate, also intervention is made in the regulation of the internal combustion engine.

Within the scope of the disclosure, the SCR catalytic converter may be integrated into a regulating structure which, apart from the SCR model, operates with a pilot controller and a regulator and which, under certain circumstances, can also be used to carry out compensation of a model. In particular, the regulating structure serves to adapt the storage capacity, sensed by the SCR model, in the case of load changes, on the premise of ensuring a sufficient conversion rate by adapting the storage capability in the SCR model, and of quickly adapting the necessary conversion rate to the real conditions.

It is generally only necessary to change the storage capability of the SCR model in the case of load changes with a large change in temperature. For the determination of the storage capability, the respective maximum storage capability and the instantaneous load of the catalytic converter disks are progressively calculated in time intervals in the SCR model. As a result, the SCR model supplies the basic data for the decision as to whether adaptation is to be performed by storage by increasing the $NH_3$ load, or removal from storage by reducing the $NH_3$ load. The decision on the basis of this basic data, and therefore as a function of the storage capability, results from a comparison of the respectively predefined emission value, in particular of the legal emission limiting value predefined as an emission value, for $NO_x$ and the $NO_x$ value which is calculated in the model and is carried out in the pilot controller.

It is therefore possible to carry out an adaptation, for example, in the case of an $NO_x$ value from the model calculation which is above the predefined emission value as a setpoint value, since too little is converted in the catalytic converter and a setpoint conversion rate which is tailored to the predefined emission value has to be reached by increasing the metered quantity of $NH_3$, that is to say by storing $NH_3$. The quantity of $NH_3$ which is to be injected is correspondingly increased for the storage by means of the pilot controller.

Generally, the quantity of $NH_3$ which is to be injected is defined by the pilot controller in such a way that the respectively predefined emission value, in particular an emission limiting value for $NO_x$ of the order of, for example, 0.67 g/kWh, which is often country-specific and is legally predefined, is complied with, wherein the quantity of $NH_3$ which is stored in the SCR model is increased or decreased in accordance with the detected deviation of the $NO_x$ value calculated in the model from the predefined emission value. Therefore, for example in the case of an excessively large conversion rate of $NO_x$ and an $NO_x$ value, which is calculated on the basis thereof in the pilot controller and which is below the predefined emission value, the injection of $NH_3$ is decreased by means of the pilot controller, that is to say due to a lack of $NH_3$ the consumption of $NH_3$ is covered by removing $NH_3$ from storage.

In the case of relatively small deviations, generally therefore in the steady-state operating mode, it is assumed that the SCR model is set correctly in terms of the storage capability of the disks. In this case, the regulator approximates the actual value measured downstream of the SCR to the calculated $NO_x$ setpoint value downstream of the catalytic converter by incremental adaptation of the respective metering quantity. The deviations arise, for example, through metering inaccuracies.

In the case of relatively small deviations of the $NO_x$ values calculated in the SCR model from the measured $NO_x$ values downstream of SCR catalytic converter, the adaptation of the sprayed-in mass of $NH_3$ is therefore superimposed by means of the regulator, and said adaptation is, under certain circumstances, performed independently of the definitions of the pilot controller in order to ensure rapid adaptation with respect to compliance of the NO emission values.

The input variables, which are processed in the pilot controller after being supplied by the SCR model, are at least mainly: NO downstream of SCR ppm, $NO_2$ downstream of SCR ppm, maximum convertible NO mol/s, maximum convertible $NO_2$ mol/s, NO converted mol/s, $NO_2$ converted mol/s, $NH_3$ max. mol storable, $NH_3$ mol stored.

In the model adjustment integrated into the regulating structure, the chronological profile of the difference between the predefined $NO_x$ emission value and the corresponding $NO_x$ value calculated in the model is determined at defined times. If these values correspond, that is to say if the $NO_x$ curves of these values plotted over time are congruent, the model is set correctly with respect to the $NH_3$ storage capability and the $NO_x$ conversion rates. If the curves are not congruent, the area between the curves is a measure of the model error. If this model error exceeds a threshold value, the model is changed with respect to the storage capability.

Since the storage capability changes only slowly with the aging of the catalytic converter, the model adjustment preferably takes place only during the removal from storage, especially since the model error is more clearly visible during removal from storage than during storage. If a model adjustment takes place, the change in the storage capability which is brought about by the aging is also determined in the SCR model with the result that according to the disclosure it is also possible to ensure that despite the maximum storage capability for $NH_3$ which is decreased by the aging drift over the operating period, a sufficient maximum conversion rate is ensured.

Within the scope of the disclosure, in the SCR model the $NO_x$ reactions are determined as chemical reactions for the SCR open-loop/closed-loop control with respect to urea as the reducing agent by means of the known main reactions presented below:

as a fast reaction as a standard reaction, and as a slow reaction.

Characteristic diagram values, determined in test bench trials for the catalytic converter material, for conversion rates and storage capability of $NH_3$ form a substantial basis for the SCR model and the sequences covered by it.

On this basis, the total conversion rate into nitrogen oxides, that is to say the $NO_x$ value downstream of the catalytic converter, is determined wherein, with respect to the individual catalytic converter disks provided in the modeling, the flow rate, the temperature, the $NO_x$ concentration and the quantity of $NH_3$ available in the disk are taken into account with particular priority.

BRIEF DESCRIPTION OF THE DRAWINGS

Further details and features of the disclosure can be found in the claims, the following explanations and the drawings. In the drawings:

DETAILED DESCRIPTION

As is known from practice and also often described in the literature, in particular the patent literature, there are in particular drive systems which are operated with diesel engines and in which exhaust gas post-treatment systems are used arranged downstream with respect to the engine by means of which certain exhaust gas components, in particular pollutants contained in the exhaust gas are to be as far as possible removed from the exhaust gas or at least made innocuous. In order to reduce the amount of nitrogen oxides contained in the oxygen-rich exhaust gas of diesel internal combustion engines, in particular what is referred to as SCR technology is used in which the nitrogen oxides are selectively reduced to form nitrogen and water using ammonia or a corresponding precursor which can be converted into ammonia.

So that this is achieved with a high conversion rate of the nitrogen oxides, in particular the temperature-dependent $NH_3$ storage capability of the catalytic converter has to be taken into account, which storage capability changes, in particular, as a function of the operating conditions of the internal combustion engine, and also the ambient conditions and over the through-flow length of the catalytic converter. These changes cannot be detected in a real fashion, in particular with acceptable expenditure. For this reason, parallel to the detection of the temperatures by measuring technology on the input side and the output side with respect to the catalytic converter, the temperature distribution therein is detected in a virtual, model-based fashion in order to obtain a picture of the temperature distribution which is as precise as possible while taking into account the temperature values which are detected by measuring technology and the temperature values which are determined virtually, and in order to be able to perform open- and/or closed-loop control of the metering in of the reducing agent, that is to say an ammonia-forming substance, also correlated to the storage behavior of the catalytic converter, in particular while taking into account said temperature distribution.

Figure 1:
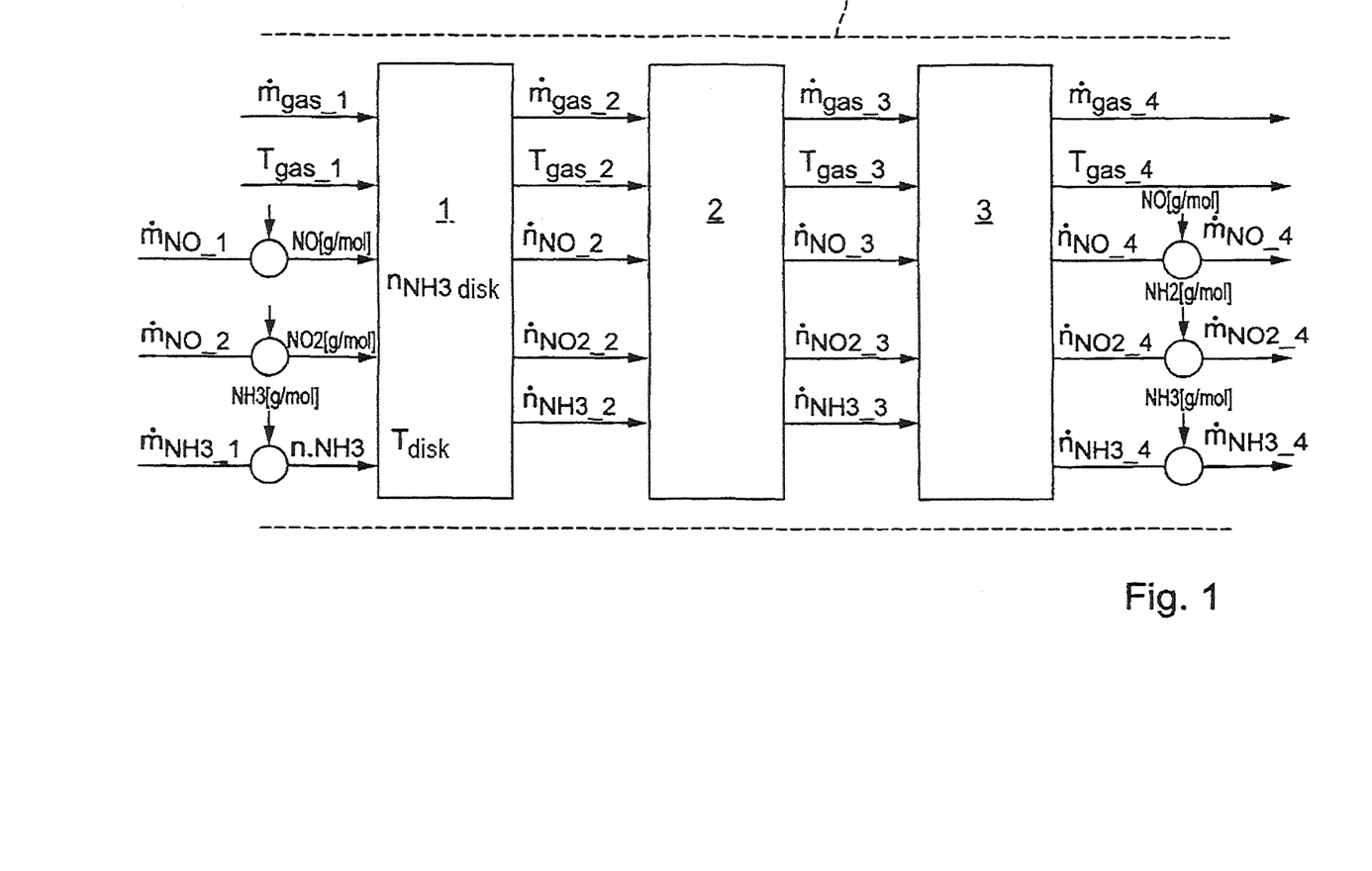
FIG. 1 is a schematic illustration of an SCR catalytic converter which is divided axially into disks in a virtual fashion as an example also of exhaust gas post-treatment units which are formed by other kinds of catalytic converters and/or particle filters.

FIG. 1 illustrates the segmentation of a catalytic converter body in a model, by axial sub-division into a relatively large number of disks, through the illustration of three disks 1 to 3 lying one behind the other in the through-flow direction of the catalytic converter, and 5 indicates, by way of dot-dashed lines, a casing which surrounds the catalytic converter body on the circumference side. In accordance with the exhaust gas flow which is directed via the catalytic converter, the disks 1 to 3 each have a mass flow $\dot{m}$ gas applied to them which corresponds to this exhaust gas flow, as the temperature Tgas of the respective disk 1 to 3 changes.

In accordance with the engine emissions and the metering in of reducing agent into the exhaust gas flow, the latter contains mass fractions m of NO, $NO_2$ and $NH_3$ to which corresponding molar amounts n correlate, said amounts changing in accordance with the respective conversion rates over the throughput through the disks 1 to 3. In accordance with the illustration, the output values of the one disk, for example disk 1, constitute the input values of the following disk, for example the disk 2. Taking into account the reactions which take place in each of the disks, a corresponding temperature Tdisk and also the molar amount $nNH_3$ in mol stored in the disk are obtained for each of the disks, wherein the temperature effect arising from the reactions in the disks is substantially less compared to the inputting of heat from the exhaust gas flow.

In a refinement of the detection of temperature for the disks, it is also possible to detect the conduction of heat between successive disks (not illustrated). The entire molar amount of $NH_3$ which is stored in the catalytic converter corresponds to the sum of the molar amounts $NH_3$ stored in the disks.

FIG. 1 models the axial temperature profile across the catalytic converter across the disks, and initially determines a respective temperature Tdisk for each of the disks, but the radial temperature distribution over each of the disks is assumed to be constant. However, in the radial direction, it is obtained in a real fashion, now in each case within the respective disk, a temperature stratification with a decrease in the temperature towards the casing 5, for which the ambient temperature in the case of regulation is significantly below the temperature of the catalytic converter.

Figure 2:
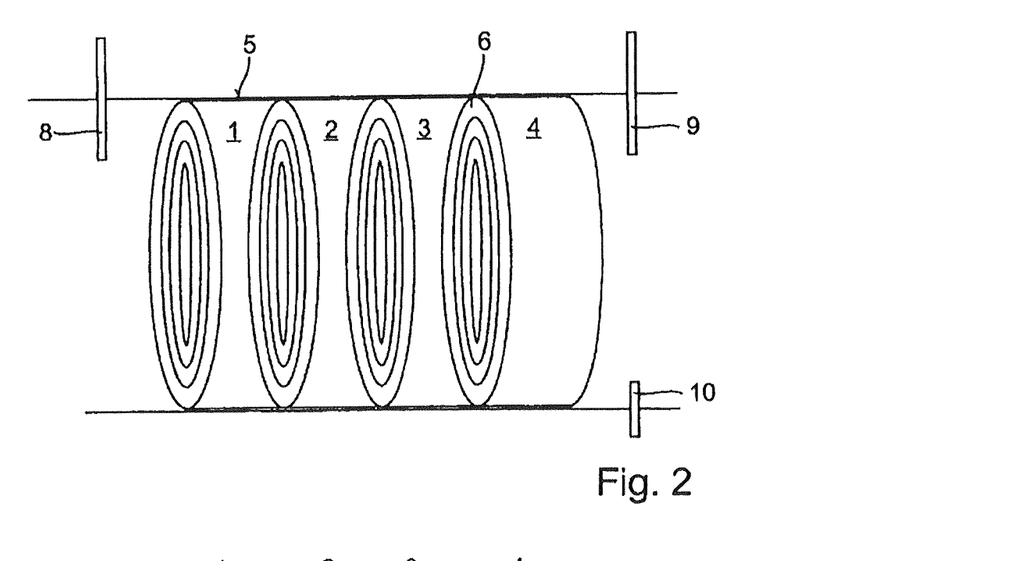
FIGS. 2 and 3 show catalytic converter disks which are segmented in cross section with respect to the direction of through-flow.
Figure 3:
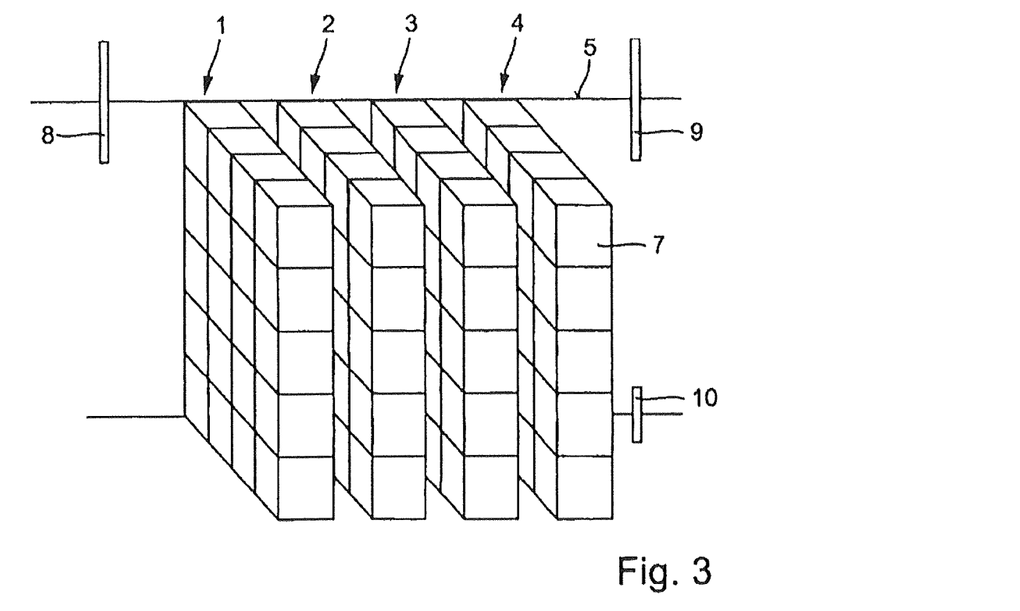

If, as in the disclosure, the radial temperature distribution is not assumed to be constant for each of the virtual disks, this requires per se for each of the disks 1 to 4 to be divided virtually into segments, as is illustrated in the schematic view in FIGS. 2 and 3. FIG. 2 shows in this regard virtual segments 6 which enclose one another radially, wherein in the illustration a central segment is enclosed by a relatively large number of annular segments.

Another type of segmentation is illustrated by FIG. 3, wherein, in contrast to the illustration in FIG. 2, a casing 5 in annular form is not provided but instead a rectangular casing 5 is provided, the disks 1 to 4 being segmented virtually into squares 7 corresponding to their cross section which is rectangular transversely with respect to the direction of through-flow.

In FIGS. 2 and 3, the arrangement of temperature detection elements, in particular sensors 8, 9, is illustrated with respect to the catalytic converter body which is respectively segmented in the model, for the purpose of detecting the temperature of the exhaust gas flow on the inflow side and outflow side of the catalytic converter body.

With respect to the radial segmentation which is provided in the model and the associated possibility of detecting the radial temperature distribution over the respective virtual disk, temperature detection can take place in different radial regions in a real fashion on the output side of the catalytic converter, as shown in FIG. 3, by two sensors 9 and 10 which are arranged in various radial positions on the output side. An averaged output-side temperature can be determined by virtue of the fact that the temperatures which are calculated for the segments are detected in accordance with their area components, and averaged. An alternative to this is to detect the exhaust gas temperature by sensor at a distance from the catalytic converter at which the emerging exhaust gases have already mixed and there is an average temperature which can be detected by one sensor.

Figure 4:
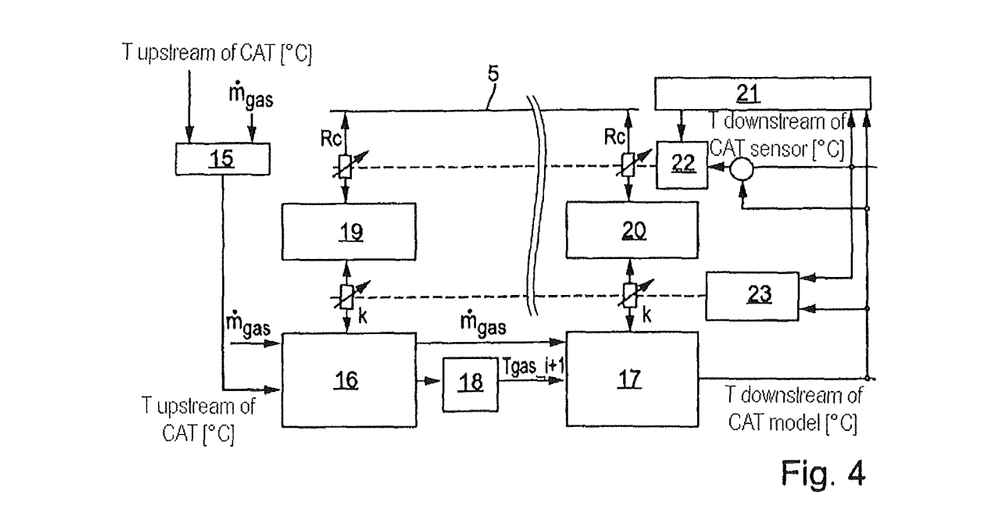
FIG. 4 shows a schematic illustration of the thermal sequences in an SCR model.

One inventive possibility for taking into account the axial and radial temperature distribution is illustrated in FIG. 4 and also provides, in particular, advantages with respect to the implementation of a model-based regulating structure, which is also referred to below.

FIG. 4 illustrates a thermal model of an SCR catalytic converter in its outlines, in which, according to FIG. 1, the temperature T upstream of the CAT and the exhaust gas mass flow ṁ gas form the input variables which are fed to a virtual heat accumulator gas mass 16 via a pole position compensation arrangement 15 for computationally compensating for the sensor inertia—and also having been verified and checked for plausibility—in which heat accumulator the heat content of the gas mass is detected in relation to the respective disk volume at the given temperature, and from which the heat transfer to the following disk owing to the transfer of the gas mass takes place, this being symbolized by the heat accumulator 17. Insofar as a rise in temperature occurs in the exhaust gas owing to exothermal reactions, this is taken into account in block 18 and leads, with respect to the heat content of the exhaust gases changing from the heat accumulator gas mass 16 to the heat accumulator gas mass 17, to a certain increase in temperature, which is sometimes even relatively strong in effect, for example in the DOC (Diesel Oxidation Catalyst), and in some cases is negligible.

The heat transfer occurs from the flowing gas mass, detected respectively on a disk-related basis, to the catalytic converter material taking into account the heat transfer coefficient k, wherein the catalytic converter material of the respective disk is illustrated symbolized as a heat accumulator 19 or 20. Oriented with the real catalytic converter, a thermal gradient results for the catalytic converter body symbolized by the heat accumulators 19, 20, with respect to the circumference of the catalytic converter, corresponding to the given temperature differences. With respect to the illustration according to FIG. 4 and the symbolic indication of the casing 5 there, a heat transfer resistance is provided with respect to the surroundings, symbolized by the heat transfer resistance $R_c$ in FIG. 4.

In the illustration of the thermal model provided by FIG. 4, it is assumed that, corresponding to the conditions in the practical operation, steady-state and non-steady-state operating phases occur and that it is possible to differentiate between these operating phases in all cases and to differentiate when the exhaust gas temperature measured at regular time intervals upstream of the exhaust gas post-treatment unit, in particular therefore upstream of the catalytic converter, changes compared to a chronological mean value over corresponding time periods. If this is not the case, it is assumed that there is a steady state, and in the other case a non-steady state. Correspondingly different control circuits are used.

Corresponding to the usually relatively small influence of the radial heat transfer, from the body thereof, in particular that is to say from the catalytic converter body, on the temperature of the exhaust gas post-treatment unit, which is embodied in particular as a catalytic converter, on the surroundings, in the steady-state case adaptation takes place by changing the heat transfer resistance $R_c$ by a regulating arrangement 22. The steady-state case is determined in the model under the conditions described above by steady-state detection indicated in the block 21. The regulating arrangement 22 takes into account the difference between the output-side temperatures T downstream of the exhaust gas post-treatment unit, with respect to an SCR catalytic converter as in the exemplary embodiment, that is to say downstream of the sensor CAT (measured) and T downstream of the model (calculated). If relevant deviations occur with respect to an exhaust gas temperature T measured over a chronological mean value of the input-side, upstream of the exhaust gas post-treatment unit, in particular upstream of the catalytic converter, the heat transfer coefficient k is changed. This is because the heat transfer coefficient k changes as a function of the flow rate of the exhaust gas, and therefore as a function of the load, and in addition the heat content of a respective storage disk, like also that of the body of the exhaust gas post-treatment unit, in particular of the catalytic converter as a whole, is influenced far more by the temperature of the through-flowing exhaust gas than by the heat transfer from the respective disk to the surroundings. The changing of the heat transfer coefficient k follows, starting from the block 23 taking into account the described dynamic factors.

Figure 5:
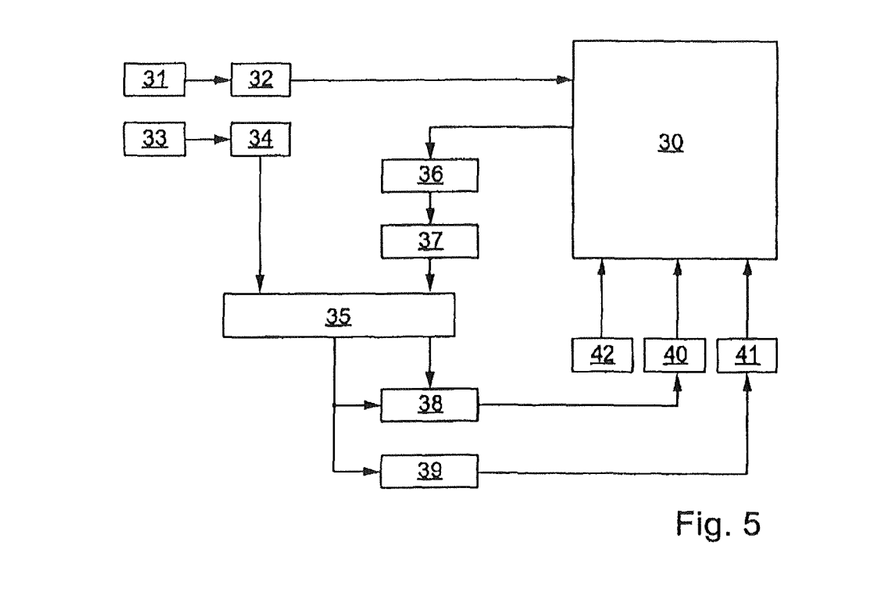
FIG. 5 shows a schematic and comprehensive illustration of a regulating structure according to the disclosure in a flow chart.

FIG. 5 shows an illustration of the sequence described above, in a block diagram, wherein again reference is also made to an SCR catalytic converter as an example of other exhaust gas post-treatment units, with the result that T downstream of CAT or T upstream of CAT also stands for T downstream of the exhaust gas purification unit or T upstream of the exhaust gas purification unit, whether measured or calculated. According to block 30, in the model calculation the dynamic correction of the measured exhaust gas temperature T, on the outlet side with respect to the exhaust gas post-treatment unit, takes place downstream of the CAT sensor, the calculation of the gas temperatures and the calculation of the temperature take place in the catalytic converter body with cross-distribution during the detection of the heat transfer to the surroundings by means of the heat transfer resistance $R_c$ and the heat transfer from the exhaust gas to the catalytic converter is calculated by the heat transfer coefficient k, wherein the model calculation is carried out from the front to the rear.

The measured, inlet-side exhaust gas temperature, denoted as T upstream of CAT, is detected in block 31 and is processed according to block 30 in the model calculation, after passing through a pole position compensation arrangement according to block 32. The measured, outlet-side exhaust gas temperature, denoted as T downstream of CAT, according to block 33 is fed to a block 35 via a pole position compensation arrangement according to block 34, in which block 35 adjustment of the measured exhaust gas temperature T downstream of CAT sensor towards the calculated exhaust gas temperature T downstream of CAT model takes place. With respect to the calculated, outlet-side exhaust gas temperature T downstream of CAT model, weighted formation of mean values takes place in block 36 taking into account the results according to block 30, which mean values are fed as a result to the block 35 via the block 37 as a calculated, outlet-side temperature T downstream of CAT sensor.

The differentiation between steady-state and non-steady-state operating behavior takes place taking into account the adjustment of measured outlet-side temperature T downstream of CAT sensor, carried out in the block 35, and the calculated outlet-side temperature T downstream of CAT model, wherein by the steady-state detection according to block 38 and the subsequent adjustment of the heat transfer resistance $R_c$ (block 40) the latter is fed as a parameter into the model calculation according to block 30. In the case of the non-steady-state detection according to block 39, provided by the adjustment according to block 35 between the measured and calculated, outlet-side temperature T downstream of CAT, the adjustment of the heat transfer coefficient k takes place in the block 41 with subsequent feeding into the model calculation according to block 30. In said model calculation, the ambient temperature T, which is made available according to block 42, is also taken into account.

Figure 6:
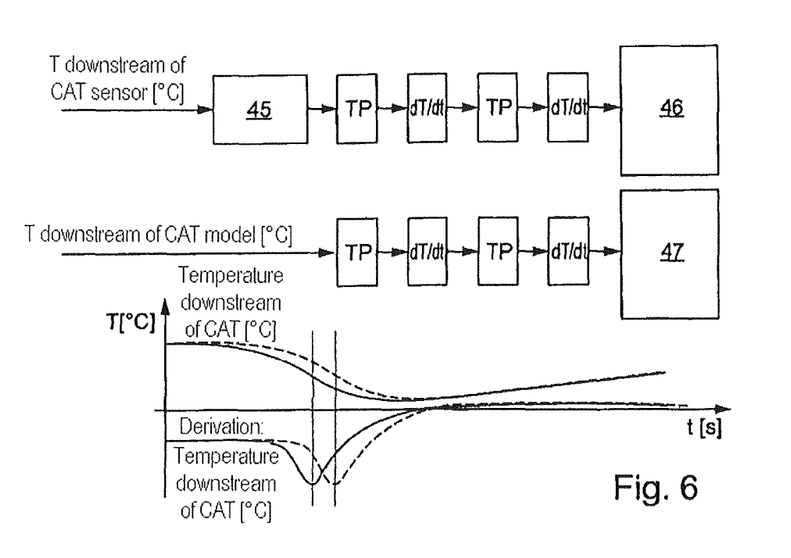
FIG. 6 shows a basic illustration of a dynamic correction with respect to the thermal sequences in an SCR model.

FIG. 6 serves to illustrate the dynamic correction, taken into account in block 30, of the temperature T, which is measured on the outlet side of the exhaust gas post-treatment unit, downstream of the CAT sensor, that is to say the temperature values which are sensed according to the sensor and therefore falsified in accordance with the inertia of the sensor. Said values are plotted (represented by dashed lines) in their profile against the time and the associated derivation, with low-pass smoothing, after pole position compensation which is symbolized in block 45 and which computationally compensates for the inertia of the sensor. For the same time period, the temperature T downstream of CAT model, determined on the model basis, that is to say calculated, is also determined in a corresponding way and represented in the diagram as a continuous line. The correction requirement is represented in the corresponding offset of the timing of the inflection points corresponding to the maximum and minimum values of the derivation curves, wherein the given chronological offset has to be minimized as part of the correction. This is done by correspondingly changing the k value with the effect of decreasing or increasing said value in the model calculation. For the correction of the k value, the latter is expediently corrected by the same order of magnitude in each case, for example approximately one percentage point plus or minus. The numerical values corresponding to the derivatives are determined in the blocks 46 and 47 and plotted in the diagram.

Figure 7:
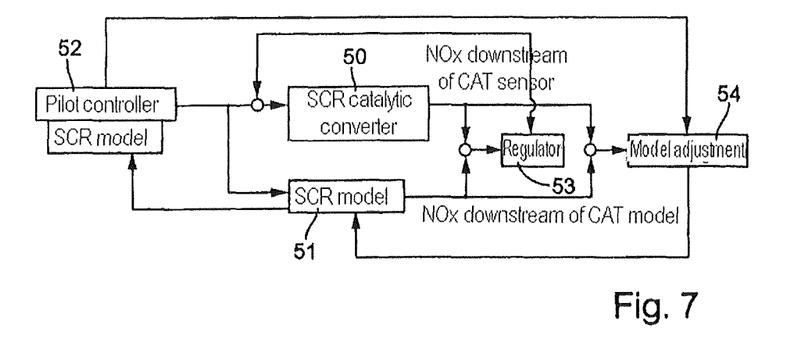
FIG. 7 shows an overview of a regulating structure in relation to an SCR catalytic converter according to the disclosure which is controlled in a model-based fashion.

By using a model-based calculation of the temperature distribution in a model of an exhaust gas purification unit, in particular by using the model-based calculation explained above, operation is carried out in a regulating structure for an exhaust gas purification unit, in particular an SCR catalytic converter according to FIG. 7.

In FIG. 7, tailored as already above to an SCR catalytic converter as an example also for other exhaust gas purification units, an SCR catalytic converter is denoted by 50, and an SCR model by 51, in particular of the type mentioned and explained above, a pilot controller by 52, a regulator by 53 and a model adjustment arrangement 54.

In the SCR model the temperature-dependent $NH_3$ storage capability is additionally taken into account, in particular in parallel with the modeled temperature calculation, as a function of the $NH_3$ concentration in the exhaust gas, in particular in a characteristic-diagram-related fashion on the basis of data determined on a test bench for the respective catalytic converter material. By taking into account this storage behavior and the main reactions represented below, the total conversion rate of $NH_3$ is determined, said conversion rate correlating to the difference between the proportion of $NO_x$ upstream of the CAT and the proportion downstream of the CAT, and by means of it the $NO_x$ value which is respectively taken as the target value, for example the emission value which is to be complied with on the basis of legal prescriptions, can therefore be determined.

The abovementioned main reactions are:

$$NO + NO_2 + 2NH_3 \rightarrow 2N_2 + 3H_2O, \qquad 1.)$$

as a fast reaction $$4NO + 4NH_3 + O_2 \rightarrow 4N_2 + 6H_2O \qquad 2.)$$

as a standard reaction, and $$6NO_2 + 8NH_3 \rightarrow 7N_2 + 12H_2O \qquad 3.)$$

as a slow reaction.

For the model calculation, it can be assumed as an approximation that the more rapid reaction is ended in each case before the slower one begins, with the result that in terms of the computational technology the reactions can be assumed to occur in succession. After the respectively more rapid reaction, the converted quantities of NO and $NO_2$ are subtracted from the initial quantities and after each reaction the quantity of $NH_3$ which is still available in the volume of a disk is determined.

With respect to the regulating structure according to FIG. 7, the SCR model 51 therefore provides a representation of the SCR catalytic converter 50 which is as accurate as possible in terms of the processed characteristic variables, such as also of the output values, in particular the $NO_x$ value.

Correspondingly, the input parameters to the SCR model relating to the exhaust gas flowing via the SCR catalytic converter 50 are NO, $NO_2$, exhaust gas mass, temperature T upstream and downstream of the CAT and $NH_3$. On the outlet side the following are detected: $NO_x$, $NO/NO_2$ converted, $NO/NO_2$ maximum converted, $NH_3$ stored and $NH_3$ maximum and stored. The calculation of the conversion requirement of $NH_3$ and the quantity of $NH_3$ which is to be stored and removed from storage takes place in the pilot controller 52, and is applied to the SCR model 51 and the SCR catalytic converter 50. The regulator 53 is assigned the function of determining any additional metering quantity to the SCR catalytic converter 50 in order to adjust the SCR catalytic converter 50 with the SCR model 51 on a case-by-case basis.

Taking as a basis the fact that the quantity of $NH_3$ which is respectively matched to the predefined emission value, that is to say $NO_x$ downstream of the CAT, and which is to be sprayed in as a reducing agent by the pilot controller on the basis of the prescriptions of the SCR model 51 and that corresponding spraying in is brought about, by the model adjustment arrangement 54 an evaluation is carried out to determine whether a relatively large deviation is present between the SCR model 51 and the SCR catalytic converter 50, and this is done for the case in which the "quantity for removal from storage is unequal to zero" in the pilot controller. If this is the case, in the model the maximum storage capability is changed, and therefore also the pilot controller is adapted for the next load change since the pilot controller 52 itself operates on the basis of data which is made available by the SCR model 51. Said data comprises: NO downstream of SCR CAT ppm, $NO_2$ downstream of SCR CAT ppm, maximum convertible NO mol/s, maximum convertible $NO_2$ mol/s, NO converted mol/s, $NO_2$ converted mol/s, $NH_3$ max mol storable and $NH_3$ mol stored. According to the definition that the model adjustment takes place only if "quantity for removal from storage is unequal to zero" is in the pilot controller, model adjustment takes place only in the phase of removal from storage.

According to the data predefined by the SCR model 51, the pilot controller adjusts the injected quantity of $NH_3$ to the effect that the respectively predefined emission value, that is to say, for example, a legal emission value, is complied with. For this purpose, in the pilot controller the output-side $NO_x$ value is calculated continuously on the basis of the data supplied by the SCR model 51 and is compared with the predefined emission value. If relatively large deviations occur, the fed-in quantity of $NH_3$ is increased or decreased by changing the quantity of $NH_3$ which is metered by the pilot controller 52 and is to be injected in the SCR model 51.

For example, an $NO_x$ value of 0.5 g/kWh which is calculated by the pilot controller 52 can bring about an excessively large rate of conversion of $NO_x$ with respect to an emission value, that is to say, for example, the legal emission value of 0.67 g/kWh. Accordingly, the injection of $NH_3$ is decreased by the pilot controller 52. If the conversion of $NO_x$ is smaller than the predefined emission value, the pilot controller 52 brings about the increase in the $NH_3$ injection quantity. The storage of $NH_3$ is performed in such a way that a risk of slip is ruled out.

The time profile between an $NO_x$ which is set in a real fashion downstream of the CAT and the $NO_x$ calculated according to the model is detected at defined times using the model adjustment arrangement 54. If there is a resulting difference between these values and if these values are plotted in a diagram as $NO_x$ values over time in curves, the area between the curves is a measure of the model error. If this model error exceeds a threshold value, the storage capability in the model is changed. Such changes are preferably performed according to the invention only during the removal from storage, since the storage capability changes only slowly due to CAT aging and model errors become significantly more visible compared to the storage. In conjunction with such a correction using the model adjustment means 54, the aging of the catalytic converter is also preferably taken into account automatically.

Whether the SCR model 51 also has to be corrected in terms of its maximum storage capability under the respective conditions, that is to say whether an increase or decrease of the storage capability is necessary, depends on the $NO_x$ values which are determined by sensor, that is to say measured. The following applies: $NO_x$ model–$NO_x$ real>0: increase the storage capability of the model, <0: decrease the storage capability of the model.

In the steady-state operating mode, in the case of relatively small deviations of the $NO_x$ values, calculated in the SCR model 51, from the measured $NO_x$ values downstream of the SCR catalytic converter 50, the regulator 53 is assigned the function of performing adaptation of the sprayed-in mass of $NH_3$ in a way which is superimposed with respect to and independently of the definitions of the pilot controller 52, in order to ensure rapid adaptation with respect to compliance of the $NO_x$ emission values.

Figure 8:
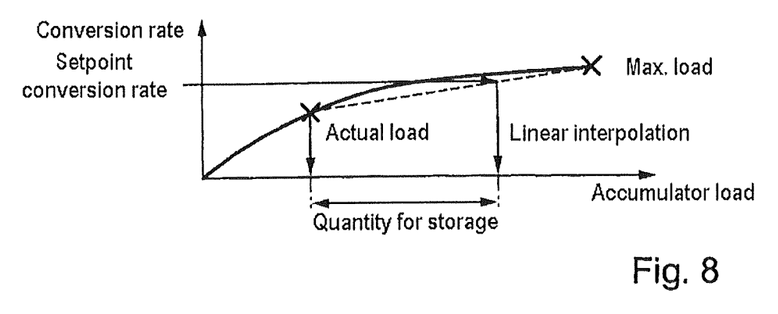
FIGS. 8 and 9 show illustrations of the graphic determination of the quantity of $NH_3$ which is stored and removed from storage in the case of a quantity of $NH_3$ which is to be stored or removed from storage in a corrective fashion by means of the model adjustment.
Figure 9:
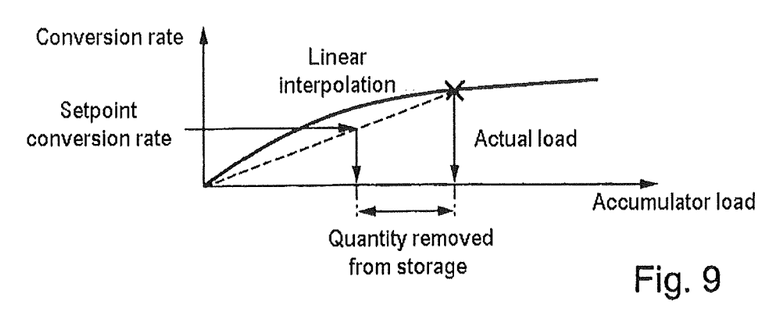

The said adaptation preferably takes place in that the conversion rate of $NO_x$ or $NH_3$ is detected over the load of the accumulator, and deviations of the actual load from the load corresponding to the setpoint conversion are determined as a measure for what quantity is to be stored or removed from storage. In the case of storage, the quantity which is to be stored corresponds to the difference between the actual load and the setpoint conversion rate of a corresponding load with respect to a linear interpolation of the load curve between the actual load value and the maximum load. In the case of removal from storage, the quantity which is to be removed from storage corresponds to the difference between the actual load and a linear interpolation of the load curve between the actual load and the passage thereof through the point of intersection of the axes, as illustrated in FIGS. 8 and 9.

The invention claimed is:
1. A method for a model, comprising:
   determining a theoretical temperature distribution of an exhaust gas post-treatment unit, wherein exhaust gas flows axially through the post-treatment unit and which the post-treatment unit is segmented at least axially in a model of the post-treatment unit, wherein the theoretical temperature distribution is determined from at least:
   (a) a theoretical axial heat transfer between the segments due at least predominantly to the exhaust gas, the radial heat transfer determined from at least a heat transfer coefficient (k) and;
(b) a theoretical radial heat transfer from a circumference of the post-treatment unit to the surroundings, the radial heat transfer determined from at least a heat transfer resistance value ($R_c$), determining a deviation of a theoretical temperature downstream of the post-treatment unit from an actual temperature downstream of the post-treatment unit, and in response to the determination of the deviation, (a) adjusting the heat transfer resistance value ($R_c$) when the model is in a steady-state operating mode, and (b) adjusting the heat transfer coefficient (k) when the model is in a non-steady state operating mode are determined based upon a variation of an exhaust gas temperature measured upstream of the post-treatment unit at predetermined and regular time intervals with respect to a chronological mean value of the exhaust gas temperature; and applying an amount of reducing agent to the post-treatment unit, the amount determined from at least the theoretical temperature distribution.

2. The method as claimed in claim 1,
wherein, for the modeling with respect to axial segmentation of the post-treatment unit is axially segmented into disks and radially segmented into rings, wherein the average calculated temperature downstream of the post-treatment unit is determined by averaging the temperatures calculated for each radial segment of the last disk in the axial direction.

3. The method as claimed in claim 1,
wherein, for a steady-state operating mode which is based on a given operating state, the given heat transfer coefficient (k) for this operating state is retained in the model calculation.

4. The method as claimed in claim 1,
wherein, for a non-steady-state operating mode which is based on a given operating state, a constant heat transfer coefficient ($R_c$) is expected in the modeling for this operating, state.

5. The method as claimed in claim 1,
wherein the heat transfer coefficient ($R_c$) is dependent on the ambient conditions of the post-treatment unit.

6. The method as claimed in claim 1,
wherein the direction of the change in the heat transfer coefficient (k), is determined at least by the derivatives of the measured and calculated average temperature profiles downstream of the post-treatment, wherein the heat transfer coefficient (k) is increased and decreased as a function of the relative timing of the inflection points which correspond to the maximum and minimum values of the derivatives.

7. The method for the model-based determination of the temperature distribution of an exhaust gas post-treatment unit using an SCR catalytic converter, as claimed in claim 1;
wherein the SCR catalytic converter is integrated into a regulating structure with at least one SCR model, a pilot controller and a regulator,
wherein a quantity of $NH_3$ which is fed to the SCR catalytic converter is determined based upon at least an emission limiting value, by the pilot controller, wherein the SCR model supplies the input variables for the pilot controller, wherein in the pilot controller the $NO_x$ value corresponding to the supplied data is continuously calculated and compared with the predefined emission value, and wherein, by adapting the respective $NH_3$ quantity which is fed to the SCR catalytic converter, the regulator approximates the $NO_x$ actual value measured downstream of the SCR catalytic converter to the a calculated $NO_x$ setpoint value downstream of the SCR catalytic converter.

8. The method as claimed in claim 7, wherein the approximation is performed incrementally in the steady-state mode in order to compensate deviations of the $NO_x$ actual value measured downstream of the SCR catalytic converter from the calculated $NO_x$ setpoint value downstream of the SCR catalytic converter.

9. The method as claimed in claim 7, wherein input variables provided for the pilot controller include at least: NO and $NO_2$ downstream of an SCR ppm, the maximum amount of NO and $NO_2$ mol/s which can be converted at the given load, the converted NO and $NO_2$ mol/s, the maximum $NH_3$ storage capacity $NH_3$ max, mol which can be stored, and the $NH_3$ storage load $NH_3$ mol stored.

10. The method as claimed in claim 7, wherein deviations which occur in a variable-dependent fashion between the $NO_x$ value determined on the basis of the input variables in the pilot controller and the predefined, emission value are taken into account by changing the supply of $NH_3$ in such a way that an increase or decrease occurs for the $NH_3$ stored in the SCR model.

11. The method as claimed in claim 7, wherein a model adjustment arrangement, in which the time sequence of the difference between measured $NO_x$ values and those determined in the model is determined as a measure of model errors, is integrated into the regulating structure.

12. The method as claimed in claim 7, wherein $NO_x$ reactions in the SCR model are determined by subsequent main reactions $$NO+NO_2+2NH_3 \rightarrow 2N_2+3H_2O, \qquad 1.)$$

as a fast reaction $$4NO+4NH_3+O_2 \rightarrow 4N_2+6H_2O \qquad 2.)$$

as a standard reaction, and $$6NO_2+8NH_3 \rightarrow 7N_2+12H_2O, \qquad 3.)$$

as a slow reaction.

* * * * *